United States Patent
Kimura et al.

(10) Patent No.: US 10,357,214 B2
(45) Date of Patent: Jul. 23, 2019

(54) PHOTON COUNTING CT APPARATUS, LIGHT DETECTION DEVICE, RADIATION DETECTION DEVICE, AND RADIATION ANALYSIS DEVICE

(71) Applicant: Toshiba Medical Systems Corporation, Otawara-shi (JP)

(72) Inventors: Shunsuke Kimura, Kawasaki (JP); Hideyuki Funaki, Shinagawa (JP); Go Kawata, Kawasaki (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 674 days.

(21) Appl. No.: 14/922,873

(22) Filed: Oct. 26, 2015

(65) Prior Publication Data
US 2016/0045176 A1 Feb. 18, 2016

Related U.S. Application Data

(63) Continuation of application No. PCT/JP2014/061848, filed on Apr. 28, 2014.

(30) Foreign Application Priority Data

Apr. 26, 2013 (JP) .................. 2013-093754

(51) Int. Cl.
*A61B 6/03* (2006.01)
*G01T 1/24* (2006.01)
(Continued)

(52) U.S. Cl.
CPC ............ *A61B 6/4241* (2013.01); *A61B 6/03* (2013.01); *A61B 6/032* (2013.01); *A61B 6/035* (2013.01);
(Continued)

(58) Field of Classification Search
CPC ......... A61B 6/032; A61B 6/42; A61B 6/4208; A61B 6/4233; A61B 6/4241; A61B 6/482; G01T 1/20; G01T 1/2006; G01T 1/2018
(Continued)

(56) References Cited

U.S. PATENT DOCUMENTS 6,426,494 B1  7/2002  Kiyota
6,858,829 B2  2/2005  Nishimura et al.
(Continued)

FOREIGN PATENT DOCUMENTS

JP  2000-200922 A  7/2000
JP  2002-84235 A   3/2002
(Continued)

OTHER PUBLICATIONS

International Search Report dated Jun. 24, 2014 for PCT/JP2014/061848 filed on Apr. 28, 2014 with English Translation.
(Continued)

*Primary Examiner* — Allen C. Ho
(74) *Attorney, Agent, or Firm* — Oblon, McClelland, Maier & Neustadt, L.L.P.

(57) ABSTRACT

According to an embodiment, a photon counting CT apparatus includes a scintillator, a photodiode array, a holder, a divider, and an image generator. The scintillator is configured to convert X-rays into light. The array includes first and second pixels. The first pixel includes a photodiode in a first range receiving the light emitted from the scintillator. The photodiode outputs an electrical signal based on the light. The second pixel includes a photodiode in a second range different from the first range. The holder is circuitry configured to hold a value of an electrical signal output by the second pixel. The divider circuitry is configured to count the number of photons of light incident on the first pixel by
(Continued)

dividing an integrated value of electrical signals output by the first pixel by the held value. The image generator is circuitry configured to reconstruct an image based on the counted number.

8 Claims, 9 Drawing Sheets

(51) Int. Cl.
| | |
|---|---|
| A61B 6/00 | (2006.01) |
| G01T 1/20 | (2006.01) |
| G01T 1/17 | (2006.01) |
| G01T 1/208 | (2006.01) |
| H04N 5/32 | (2006.01) |

(52) U.S. Cl.
CPC .............. *A61B 6/42* (2013.01); *A61B 6/4208* (2013.01); *A61B 6/4233* (2013.01); *A61B 6/482* (2013.01); *A61B 6/5205* (2013.01); *G01T 1/17* (2013.01); *G01T 1/20* (2013.01); *G01T 1/208* (2013.01); *G01T 1/2018* (2013.01); *A61B 6/4035* (2013.01); *A61B 6/4042* (2013.01); *A61B 6/463* (2013.01); *A61B 6/481* (2013.01); *A61B 6/5258* (2013.01); *A61B 6/54* (2013.01); *H04N 5/32* (2013.01)

(58) Field of Classification Search
USPC ............................ 378/19, 98.8; 250/370.09
See application file for complete search history.

(56) References Cited

U.S. PATENT DOCUMENTS

| | | | | |
|---|---|---|---|---|
| 7,260,174 | B2 * | 8/2007 | Hoffman | A61B 6/032 250/363.09 |
| 7,528,458 | B2 * | 5/2009 | Wilson | H01L 27/1446 257/443 |
| 7,723,694 | B2 * | 5/2010 | Frach | G01T 1/1642 250/370.11 |
| 7,885,372 | B2 * | 2/2011 | Edic | A61B 6/032 378/158 |
| 7,970,096 | B2 * | 6/2011 | Pavlovich | A61B 6/032 378/156 |
| 7,970,291 | B2 * | 6/2011 | Nagakubo | H04B 10/6911 250/214 A |
| 8,198,577 | B2 * | 6/2012 | Dierickx | G01T 1/247 250/214 DC |
| 8,213,566 | B2 * | 7/2012 | Roessl | A61B 5/4869 378/5 |
| 8,338,773 | B2 * | 12/2012 | Eldesouki | G01J 1/46 250/208.1 |
| 8,442,184 | B2 * | 5/2013 | Forthmann | A61B 6/032 378/5 |
| 8,476,594 | B2 * | 7/2013 | Frach | G01T 1/2018 250/363.03 |
| 8,581,200 | B2 * | 11/2013 | Engel | G01T 1/2928 250/370.09 |
| 8,619,943 | B2 * | 12/2013 | Flohr | A61B 6/032 378/19 |
| 8,716,643 | B2 * | 5/2014 | Eldesouki | H01L 27/14601 250/208.1 |
| 8,859,944 | B2 * | 10/2014 | Eldesouki | H04N 5/3745 250/207 |
| 8,891,845 | B2 * | 11/2014 | Ogawa | A61B 6/14 382/128 |
| 8,921,754 | B2 * | 12/2014 | Frach | G01T 1/2018 250/214 AG |
| 8,988,267 | B1 * | 3/2015 | Kimura | G01T 1/2928 341/155 |
| 9,044,189 | B2 * | 6/2015 | Flohr | A61B 6/032 |
| 9,050,051 | B2 * | 6/2015 | Nakatsugawa | A61B 6/4233 |
| 9,052,266 | B2 * | 6/2015 | Miyazaki | A61B 6/4241 |
| 9,055,244 | B2 * | 6/2015 | Nishihara | H04N 5/32 |
| 9,109,953 | B2 * | 8/2015 | Sasaki | G01J 1/44 |
| 9,113,839 | B2 * | 8/2015 | Morton | A61B 6/032 |
| 9,116,248 | B2 * | 8/2015 | Abenaim | A61B 6/032 |
| 9,146,326 | B2 * | 9/2015 | Kuwabara | G01T 1/17 |
| 9,160,939 | B2 * | 10/2015 | Funaki | H03M 1/145 |
| 9,204,849 | B2 * | 12/2015 | Kurokawa | G01T 1/2018 |
| 9,217,795 | B2 * | 12/2015 | Hansen | G01T 1/248 |
| 9,250,333 | B2 * | 2/2016 | Okada | G01N 23/04 |
| 9,259,201 | B2 * | 2/2016 | Sato | A61B 6/4233 |
| 9,265,467 | B2 * | 2/2016 | Kamiya | A61B 6/5241 |
| 9,274,235 | B2 * | 3/2016 | Kang | G01N 23/04 |
| 9,316,749 | B2 * | 4/2016 | Okada | G01T 1/2018 |
| 9,322,928 | B2 * | 4/2016 | Iwakiri | A61B 6/4233 |
| 9,335,422 | B2 * | 5/2016 | Oda | G01T 1/17 |
| 9,344,661 | B2 * | 5/2016 | Saito | G01T 1/208 |
| 9,354,331 | B2 * | 5/2016 | Sagoh | A61B 6/032 |
| 9,417,339 | B2 * | 8/2016 | Spahn | G01T 1/247 |
| 9,423,515 | B2 * | 8/2016 | Roessl | G01T 1/241 |
| 9,433,391 | B2 * | 9/2016 | Miyazaki | A61B 6/4241 |
| 9,462,990 | B2 * | 10/2016 | Kuwabara | A61B 6/54 |
| 9,480,444 | B2 * | 11/2016 | Kappler | A61B 6/032 |
| 9,517,045 | B2 * | 12/2016 | Kang | G01N 23/087 |
| 9,538,107 | B2 * | 1/2017 | Chappo | A61B 6/032 |
| 9,572,540 | B2 * | 2/2017 | Zhang | G01T 1/242 |
| 9,579,075 | B2 * | 2/2017 | Besson | G01T 1/2985 |
| 9,579,076 | B2 * | 2/2017 | Tajima | H05G 1/44 |
| 9,595,101 | B2 * | 3/2017 | Kato | G06T 11/005 |
| 9,619,730 | B2 * | 4/2017 | Pavlovich | A61B 6/032 |
| 9,629,601 | B2 * | 4/2017 | Tajima | A61B 6/4208 |
| 9,662,077 | B2 * | 5/2017 | Moriyasu | A61B 6/4241 |
| 9,668,331 | B2 * | 5/2017 | Takahashi | H04N 5/32 |
| 9,693,743 | B2 * | 7/2017 | Arakita | G01T 1/1606 |
| 9,750,471 | B2 * | 9/2017 | Schirra | A61B 6/4241 |
| 9,750,477 | B2 * | 9/2017 | Kitagawa | A61B 6/542 |
| 9,780,128 | B2 * | 10/2017 | Tajima | H05G 1/38 |
| 9,793,305 | B2 * | 10/2017 | Tajima | G01T 1/2985 |
| 9,808,210 | B2 * | 11/2017 | Yamazaki | A61B 6/032 |
| 9,826,943 | B2 * | 11/2017 | Bruder | A61B 6/027 |
| 9,848,845 | B2 * | 12/2017 | Tajima | H04N 5/32 |
| 9,892,521 | B2 * | 2/2018 | Enomoto | A61B 6/4233 |
| 9,924,916 | B2 * | 3/2018 | Kato | A61B 6/482 |
| 10,004,464 | B2 * | 6/2018 | Brady | G01N 23/046 |
| 10,010,303 | B2 * | 7/2018 | Konno | A61B 6/032 |
| 10,074,679 | B2 * | 9/2018 | Tajima | A61B 6/4233 |
| 2002/0085667 | A1 | 7/2002 | Miller | |
| 2006/0056581 | A1 | 3/2006 | Hoffman et al. | |
| 2008/0138092 | A1 | 6/2008 | Nagakubo | |
| 2013/0010921 | A1 | 1/2013 | Sagoh et al. | |
| 2015/0076357 | A1 | 3/2015 | Frach | |

FOREIGN PATENT DOCUMENTS

| | | |
|---|---|---|
| JP | 2003-000578 A | 1/2003 |
| JP | 2003-37283 A | 2/2003 |
| JP | 2011-165714 A | 6/2008 |
| JP | 2009-18154 A | 1/2009 |
| JP | 2010-112866 A | 5/2010 |
| JP | 2011-165714 A | 8/2011 |
| JP | 2012-519843 A | 8/2012 |
| WO | WO 2012/173206 A1 | 12/2012 |

OTHER PUBLICATIONS

Written Opinion dated Jun. 24, 2014 for PCT/JP2014/061848 filed on Apr. 28, 2014.
Japanese Office Action dated Aug. 8, 2017 in Japanese Patent Application No. 2013-093754.
Office Action dated Feb. 7, 2017 in Japanese Patent Application No. 2013-093754.

* cited by examiner

PHOTON COUNTING CT APPARATUS, LIGHT DETECTION DEVICE, RADIATION DETECTION DEVICE, AND RADIATION ANALYSIS DEVICE

CROSS-REFERENCE TO RELATED APPLICATIONS

This application is a continuation of PCT international Application Ser. No. PCT/JP2014/061848, filed on Apr. 28, 2014, which designates the United States and which claims the benefit of priority from Japanese Patent Application No. 2013-093754, filed on Apr. 26, 2013; the entire contents of which are incorporated herein by reference.

FIELD

Embodiments described herein relate generally to a photon counting CT apparatus, a light detection device, a radiation detection device, and a radiation analysis device.

BACKGROUND

As one of light detection devices, a light detection device is known that uses an avalanche photodiode array. This light detection device has a feature capable of detecting light at a single photon level. The light detection device has a problem in that multiplication factors of the avalanche photodiodes vary with a substrate temperature and an ambient temperature. To avoid such a problem, it is known to change reverse voltages applied to the avalanche photodiodes in accordance with a temperature.

For changing the reverse voltages applied to the avalanche photodiodes in accordance with a temperature, a temperature sensor, a temperature sensor driving circuit, and a bias voltage change circuit, and the like are required, thereby having a problem in that the structure is complicated.

DETAILED DESCRIPTION

According to an embodiment, a photon counting CT apparatus includes an X-ray tube, a scintillator, a photodiode array, a holder, a divider, and an image generator. The X-ray tube is configured to generate X-rays. The scintillator is configured to convert the X-rays generated by the X-ray tube into light and emit the light. The photodiode array includes a first pixel and a second pixel. The first pixel includes a photodiode that is in a first range serving as a range where the light emitted from the scintillator is received. The photodiode outputs an electrical signal on the basis of the light. The second pixel includes a photodiode that is in a second range located at a different position from a position of the first range. The holder is circuitry configured to hold a value of an electrical signal output by the second pixel. The divider is circuitry configured to count the number of photons of light incident on the first pixel by dividing an integrated value of electrical signals output by the first pixel by the value of the electrical signal held by the holder. The image generator is circuitry configured to reconstruct an image on the basis of the counted number of photons of light.

The following describes a light detection device 100 according to an embodiment with reference to the accompanying drawings.

Figure 1:
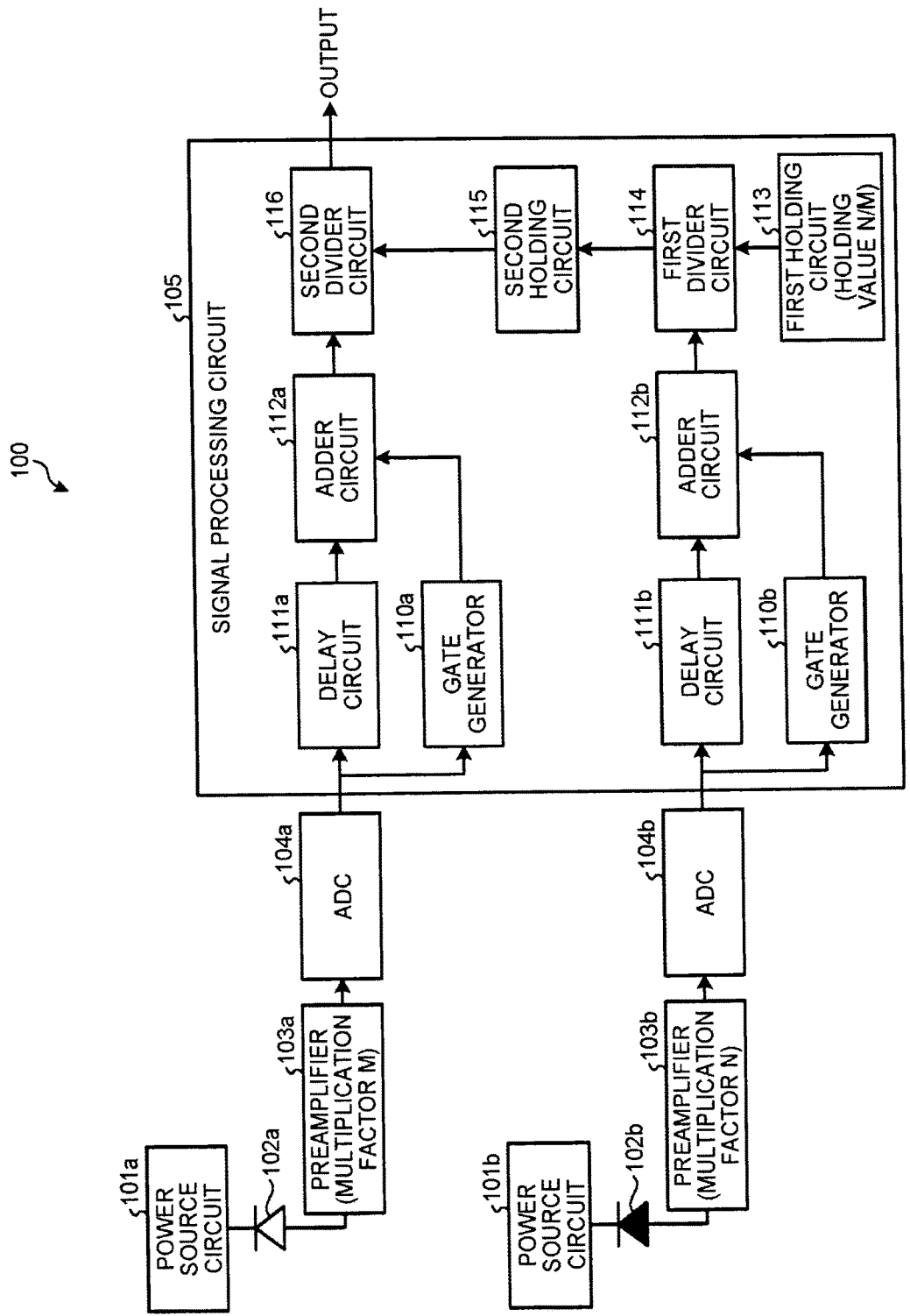
FIG. 1 is a configuration diagram schematically and exemplarily illustrating a structure of a light detection device according to an embodiment.

FIG. 1 is a configuration diagram schematically and exemplarily illustrating a structure of the light detection device 100 according to the embodiment. As illustrated in FIG. 1, the light detection device 100 includes power source circuits 101a and 101b, a light sensitive avalanche photodiode (APD) 102a, a light insensitive avalanche photodiode (APD) 102b, preamplifiers 103a and 103b, AD converters (ADCs) 104a and 104b, and a signal processing circuit 105. One or more of avalanche photodiodes 102a and one or more of avalanche photodiodes 102b are arranged in an avalanche photodiode array 102, which is described later.

The power source circuit 101a applies a voltage to the APD 102a so as to cause the APD 102a to operate in a Geiger mode in which a reverse voltage is set to be equal to or larger than a breakdown voltage. The power source circuit 101b applies a voltage to the APD 102b so as to cause the APD 102b to operate in the Geiger mode in which the reverse voltage is set to be equal to or larger than the breakdown voltage. The power source circuits 101a and 101b may be used as a common power source.

The APD 102a forms an APD pixel (image element) that is light sensitive and individually operates in the Geiger mode. The APD 102b forms an APD pixel (image element) that is light insensitive and individually operates in the Geiger mode. The APDs 102a and 102b are two dimensionally arranged so as to form the avalanche photodiode array 102. The APDs 102a and 102b are, thus, under the influence of the same environmental temperature.

Figure 2:
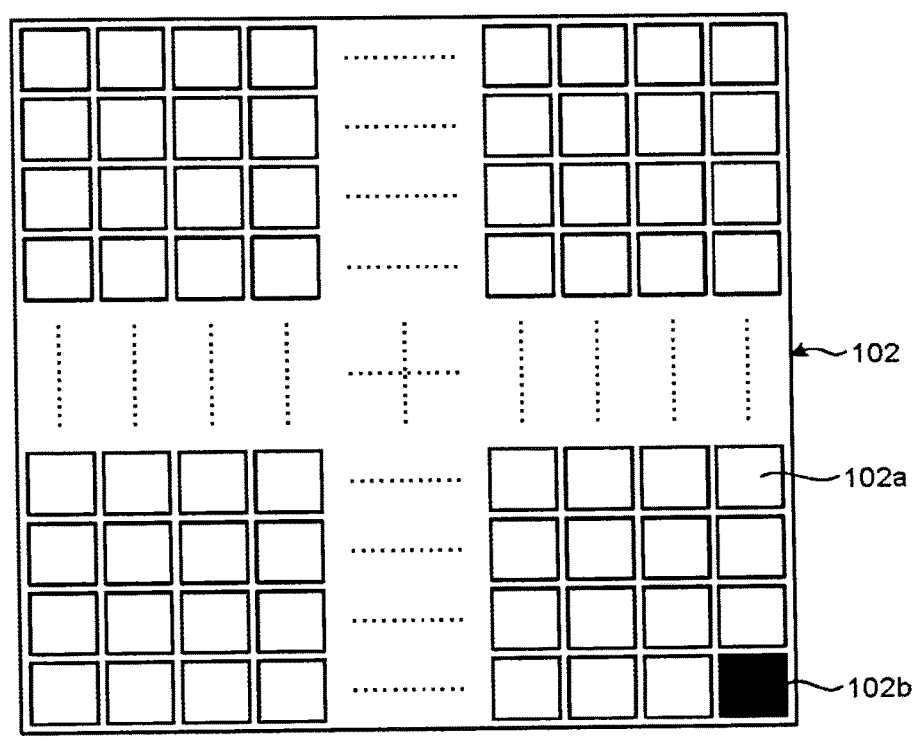
FIG. 2 is a top view of an avalanche photodiode array.

FIG. 2 is a top view of the avalanche photodiode array 102. The avalanche photodiode array 102 outputs charges generated in accordance with the number of photons of visible light received via a scintillator (a phosphor 130, refer to FIG. 9), which is not illustrated, as a current pulse via quench resistors, which are not illustrated in FIG. 1. As illustrated in FIG. 2, the avalanche photodiode array 102 includes a plurality of (e.g., about hundreds to thousands pieces of) APDs 102a and a single APD 102b. The APD 102b may be set at any position in the avalanche photodiode array 102.

Upon receiving photons of visible light, the APD 102a outputs a one photon equivalent current pulse. All of the APDs 102a are connected in parallel with one another. As a result, the current pulses output by the respective APDs 102a are superimposed to form a single current pulse. The avalanche photodiode array 102 outputs, to the preamplifier 103a, the current pulse having an area approximately proportional to the number of APDs 102a on which photons are incident. The number of APDs 102a on which photons are incident is equivalent to the number of photons of incident visible light. The area of the current pulse with respect to a temporal direction is proportional to the number of APDs 102a on which photons are incident, i.e., the total amount of generated charges.

The APD 102b is covered with a metal or the like (e.g., on the incident side of the phosphor 130) such that no visible light is incident on the APD 102b. The APD 102b is configured to output a current pulse independently from the APDs 102a. The avalanche photodiode generates a current pulse (i.e., noise or thermal noise) even without incident photons. For example, the avalanche photodiode generates a current pulse by thermal excitation. The multiplication factor of the avalanche photodiode varies with a substrate temperature, an ambient temperature, and the like, as described above. Because the APD 102b is caused to operate in the Geiger mode, the APD 102b outputs a current pulse that has a one photon equivalent waveform height and varies in accordance with an ambient temperature (or a substrate temperature and the like) to the preamplifier 103b at a high multiplication factor (105 to 106) with a certain probability.

The preamplifier 103a amplifies the current pulse output by the APDs 102a to M times and outputs the result to the ADC 104a as a voltage pulse. The preamplifier 103b amplifies the current pulse output by the APD 102b to N times and outputs the result to the ADC 104b as a voltage pulse. The value of M is set in accordance with the number of APDs 102a. The value of N is set to a value larger than the value of M so as to be able to AD convert 1 p.e. pulse, for example.

The ADC 104a AD converts the voltage pulse output by the preamplifier 103a, and outputs the voltage values after conversion to the signal processing circuit 105. The ADC 104b AD converts the voltage pulse output by the preamplifier 103b and outputs the voltage values after conversion to the signal processing circuit 105.

The signal processing circuit 105 includes gate generators 110a and 110b, delay circuits 111a and 111b, adder circuits 112a and 112b, a first holding circuit 113, a first divider circuit 114, a second holding circuit 115, and a second divider circuit 116.

The gate generator 110a receives the voltage values (AD values) output by the ADC 104a, forms a differentiated waveform from the voltage values, and produces a gate signal (gate) having an arbitrary threshold. The gate signal, which is used for measuring the voltage pulse, specifies the start and the end of integration of the voltage pulses. The gate generator 110b receives the voltage values (AD values) output by the ADC 104b, forms the differentiated waveform from the voltage values, and produces the gate signal (gate) having an arbitrary threshold.

The delay circuit 111a receives the voltage values (AD values) output by the ADC 104a, delays the voltage values so as to enable integration to be performed on at least one voltage pulse, and outputs the delayed voltage values to the adder circuit 112a. The delay circuit 111b receives the voltage values (AD values) output by the ADC 104b, delays the voltage values so as to enable integration to be performed on at least one voltage pulse, and outputs the delayed voltage values to the adder circuit 112b.

The adder circuit 112a adds the voltage values received from the delay circuit 111a in accordance with the gate signal produced by the gate generator 110a, and outputs the result to the second divider circuit 116. The adder circuit 112b adds the voltage values received from the delay circuit 111b in accordance with the gate signal produced by the gate generator 110b, and outputs the result to the first divider circuit 114.

The gate generator 110a, the delay circuit 111a, and the adder circuit 112a form an integration circuit that integrates one voltage pulse (current pulse having an area approximately proportional to the number of photons incident on the avalanche photodiode array 102) output by the ADC 104a.

The gate generator 110b, the delay circuit 111b, and the adder circuit 112b form an integration circuit that integrates one voltage pulse (current pulse having a one photon equivalent area) output by the ADC 104b.

The first holding circuit 113 holds a holding value N/M and outputs the holding value to the first divider circuit 114. The value of N/M has the same bit number as the ADCs 104a and 104b.

The first divider circuit 114 divides the current pulse that is output by the adder circuit 112b and that has a one photon equivalent area by the holding value N/M, and outputs the division result to the second holding circuit 115. The result of the division by the first divider circuit 114 is M times of the current pulse output by the APD 102b.

The second holding circuit 115 holds the result of the division (division result) by the first divider circuit 114, and outputs the holding result to the second divider circuit 116.

The second divider circuit 116 divides the voltage pulse (voltage pulse having a waveform height approximately proportional to the number of photons incident on the avalanche photodiode array 102) output by the adder circuit 112a by the division result received from the second holding circuit 115, and outputs the division result. The second divider circuit 116 calculates the number of photons incident on the avalanche photodiode array 102 by dividing the total sum (integrated value) of the current pulses output by all of the APDs 102a under the influence of the same environmental temperature by the current pulse output by the APD 102b. The APD 102a and the APD 102b are under the influence of the same environmental temperature. As a result, the number of photons calculated by the second divider circuit 116 is constant regardless of the temperature.

The light detection device 100 is provided with a phosphor, which is not illustrated, in a front stage of the avalanche photodiode array 102, and detects the number of photons generated by the phosphor in accordance with energy of radiation incident on the phosphor. The light detection device 100 is a radiation detection device that detects radiation.

Figure 3:
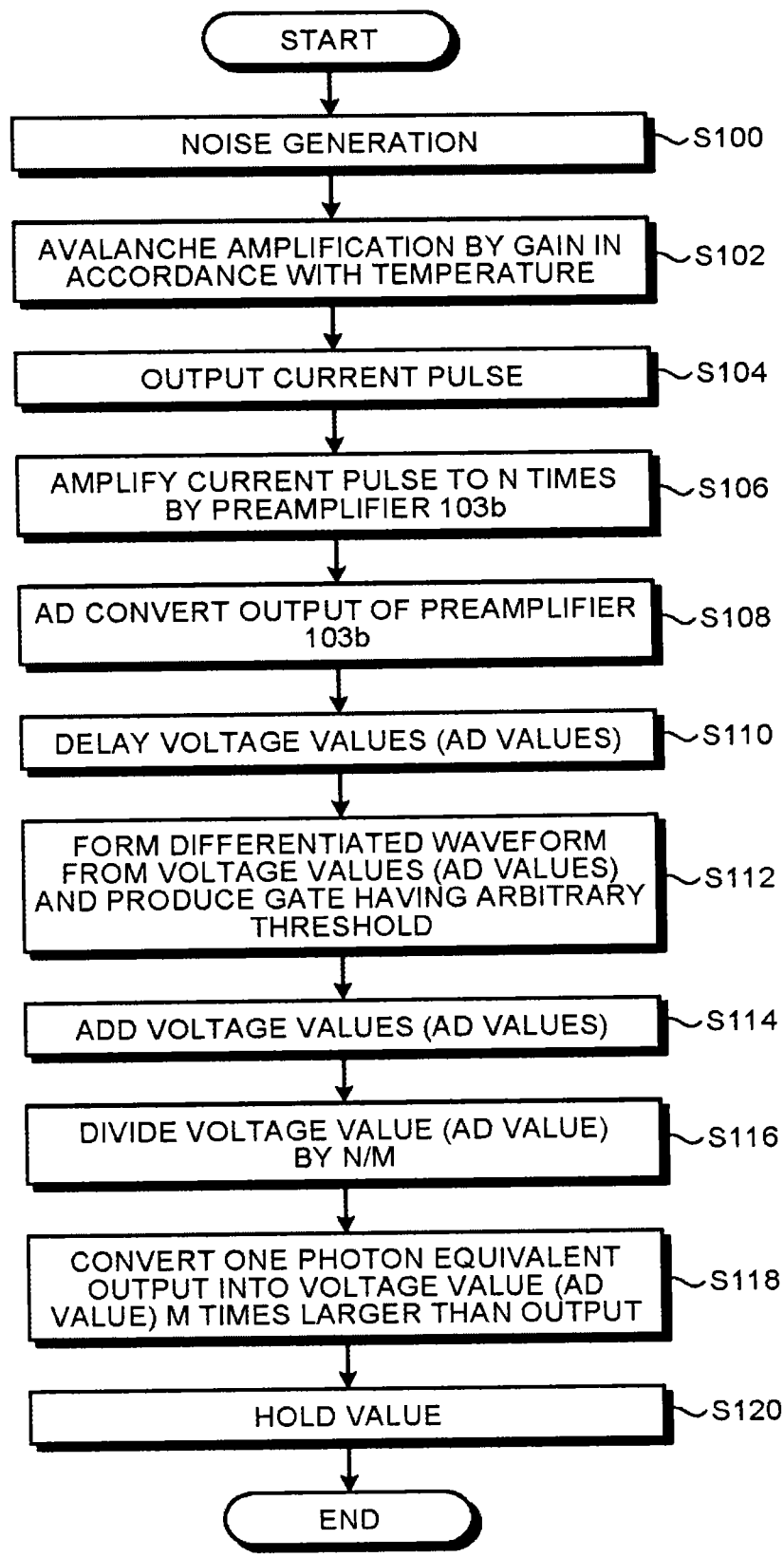
FIG. 3 is a flow chart illustrating processing performed by the light detection device until a second holding circuit holds a value corresponding to noise.

The following describes the operation of the light detection device 100. FIG. 3 is a flowchart illustrating processing performed by the light detection device 100 until the second holding circuit 115 holds the value corresponding to a voltage pulse (noise) output by the APD 102b without incident photons.

As illustrated in FIG. 3, at step 100 (S100), the APD 102b generates noise (carriers serving as a source of noise) with a certain probability due to thermal excitation and the like.

At step 102 (S102), the APD 102b performs avalanche amplification (multiplication) by a gain according to the temperature.

At step 104 (S104), the APD 102b outputs a one photon equivalent current pulse.

At step 106 (S106), the preamplifier 103b amplifies the current pulse to N times and converts the amplified current pulse into a voltage pulse.

At step 108 (S108), the ADC 104b performs AD conversion on the output of the preamplifier 103b, and outputs the voltage values after conversion.

At step 110 (S110), the delay circuit 111b delays the voltage values (AD values) output by the ADC 104b.

At step 112 (S112), the gate generator 110b forms the differentiated waveform from the voltage values (AD values) output by the ADC 104b, and produces the gate having an arbitrary threshold.

At step 114 (S114), the adder circuit 112b adds the voltage values (AD values) in accordance with the gate produced by the gate generator 110b.

At step 116 (S116), the first divider circuit 114 divides the resulting voltage value (AD value) added by the adder circuit 112b by N/M.

At step 118 (S118), the first divider circuit 114 converts the one photon equivalent output by the APD 102b into the voltage value (AD value) M times larger than the output, as the result of the processing at S116.

At step 120 (S120), the second holding circuit 115 holds the value obtained by the first divider circuit 114 as the one photon equivalent voltage value (AD value).

Figure 4:
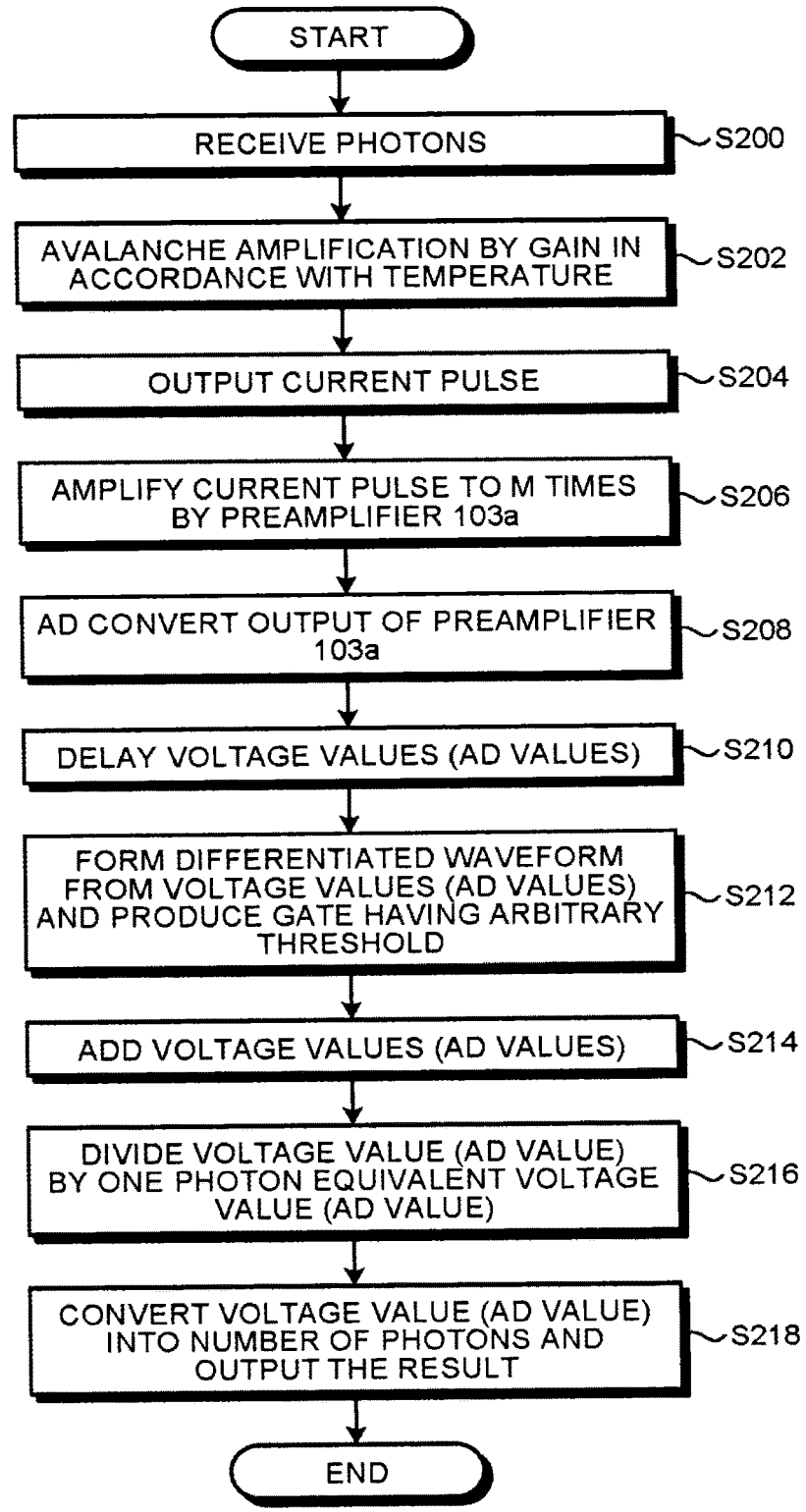
FIG. 4 is a flowchart illustrating processing performed by the light detection device for calculating the number of photons incident on the avalanche photodiode array.

FIG. 4 is a flowchart illustrating processing performed by the light detection device 100 for calculating the number of photons incident on the avalanche photodiode array 102.

As illustrated in FIG. 4, at step 200 (S200), the avalanche photodiode array 102 receives visible light. Some of the APDs 102a receive photons (particles of light).

At step 202 (S202), the APDs 102a on which photons are incident perform avalanche amplification (multiplication) by a gain according to the temperature.

At step 204 (S204), the APD 102a on which photons are incident outputs a one photon equivalent current pulse.

At step 206 (S206), the preamplifier 103a amplifies, to M times, a current pulse obtained by superimposing the current pulses output by the respective APDs 102a on which photons are incident, and converts the amplified current pulse into a voltage pulse.

At step 208 (S208), the ADC 104a performs AD conversion on the output of the preamplifier 103a, and outputs the voltage values after conversion.

At step 210 (S210), the delay circuit 111a delays the voltage values (AD values) output by the ADC 104a.

At step 212 (S212), the gate generator 110a forms the differentiated waveform from the voltage values (AD values) output by the ADC 104a, and produces the gate having an arbitrary threshold.

At step 214 (S214), the adder circuit 112a adds the voltage values (AD values) in accordance with the gate produced by the gate generator 110a.

At step 216 (S216), the second divider circuit 116 divides the resulting voltage value (AD value) added by the adder circuit 112a by the one photon equivalent voltage value (AD value) held by the second holding circuit 115.

At step 218 (S218), the second divider circuit 116 deems (converts) the result (voltage value) of the division by the processing at S216 as (into) the number of photons, and outputs the result.

Figure 5:
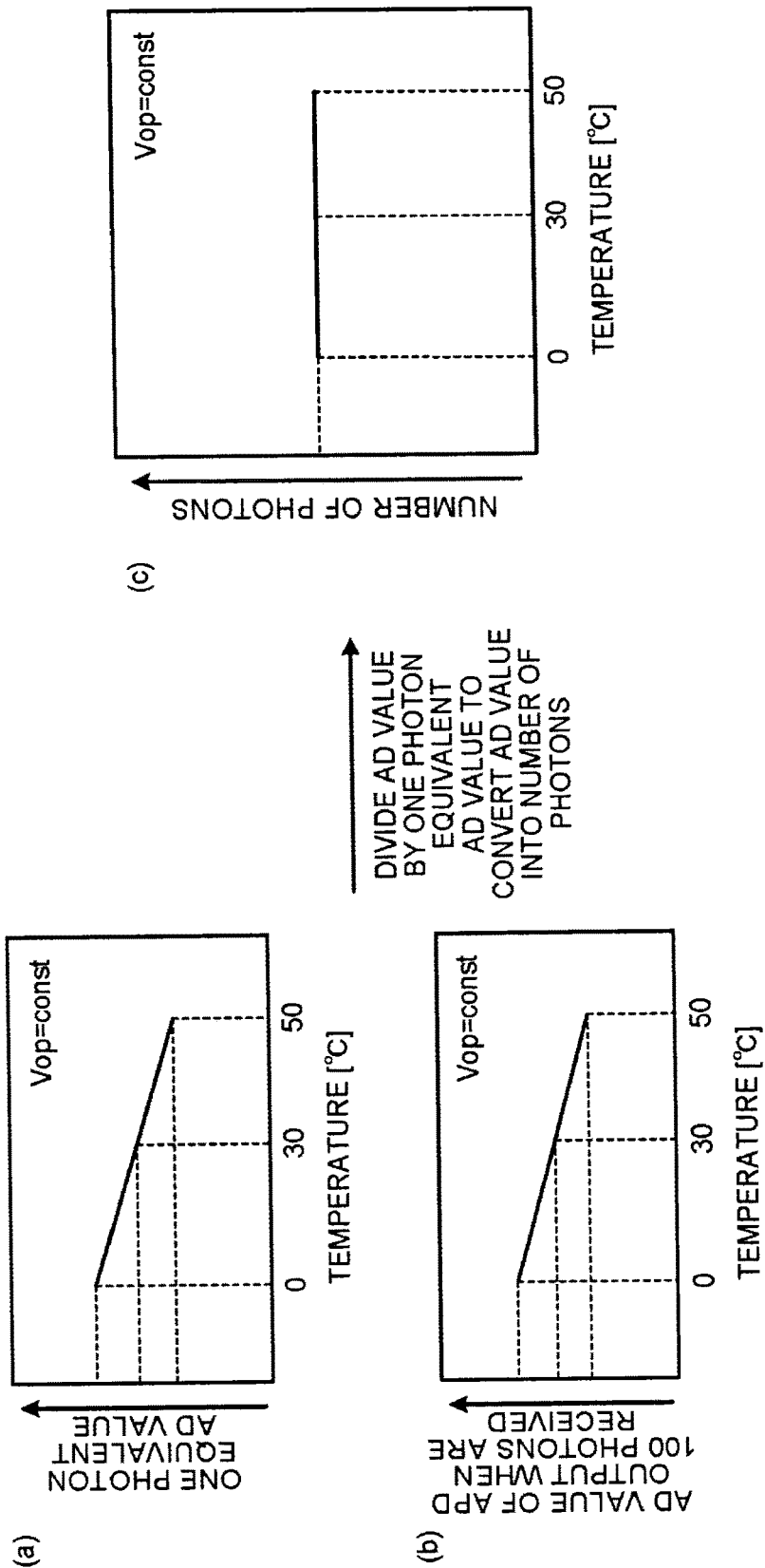
FIG. 5 is a graph illustrating an effect produced by the operation of the light detection device according to the embodiment.

FIG. 5 is a graph illustrating an effect produced by the operation of the light detection device 100. FIG. 5 illustrates an example where 100 APDs 102a receive photons out of the APDs 102a included in the avalanche photodiode array 102. Each reverse voltage (Vop) applied to the APDs 102a and the APD 102b is constant. FIG. 5(a) illustrates the one photon equivalent AD value (output of the adder circuit 112b) that varies in accordance with a temperature change. FIG. 5(b) illustrates the AD value (output of the adder circuit 112a) when 100 photons are received. The AD value varies in accordance with a temperature change.

The APD 102b outputs a current pulse due to noise caused by thermal excitation, for example, although the APD 102b is light insensitive. It can be deemed that this current pulse is equal to the current pulse output when one photon is incident on the APD 102a. When the second divider circuit 116 divides the output of the adder circuit 112a by the output of the adder circuit 112b (after the division by the first divider circuit 114), the number of photons calculated by the light detection device 100 is constant regardless of the temperature if the number of photons incident on the avalanche photodiode array 102 is the same, as illustrated in FIG. 5(c).

In this way, the light detection device 100 divides the area of the current pulse output by all of the APDs 102a under the influence of the same environmental temperature by the area of the one photon equivalent current pulse output by the APD 102b, thereby making it possible to calculate the number of photons incident on the avalanche photodiode array 102 regardless of an environmental temperature and readily compensate the temperature characteristics of the multiplication factors of the avalanche photodiodes.

The light detection device 100 can readily compensate the temperature characteristics of the multiplication factors of the avalanche photodiodes even when a temperature sensor, a temperature sensor driving circuit, a bias voltage change circuit, and the like are not provided. In addition, the light detection device 100 calculates the number of incident photons. The variance in the multiple avalanche photodiodes arranged in parallel with one another, thus, does not need to be corrected. Furthermore, the light detection device 100 does not need to correct changes in temperature and power source voltage.

The light detection device 100 may preliminarily store the output, which changes in accordance with an environmental temperature, of the APD 102b as a reference table (reference APD output value table) used for a reference of the one photon equivalent voltage value associated with each temperature (environmental temperature). For example, the signal processing circuit 105 includes a storage (not illustrated), in which the reference table is stored. The signal processing circuit 105 also saves (stores) therein time series data of the voltage values corresponding to the output of the APD 102a in association with the environmental temperature measured by a thermometer, which is not illustrated. In this case, the signal processing circuit 105 may be a corrector that corrects the time series data of the voltage values corresponding to the output of the APD 102a using the environmental temperature associated with the time series data and the reference table.

Modification

Figure 6:
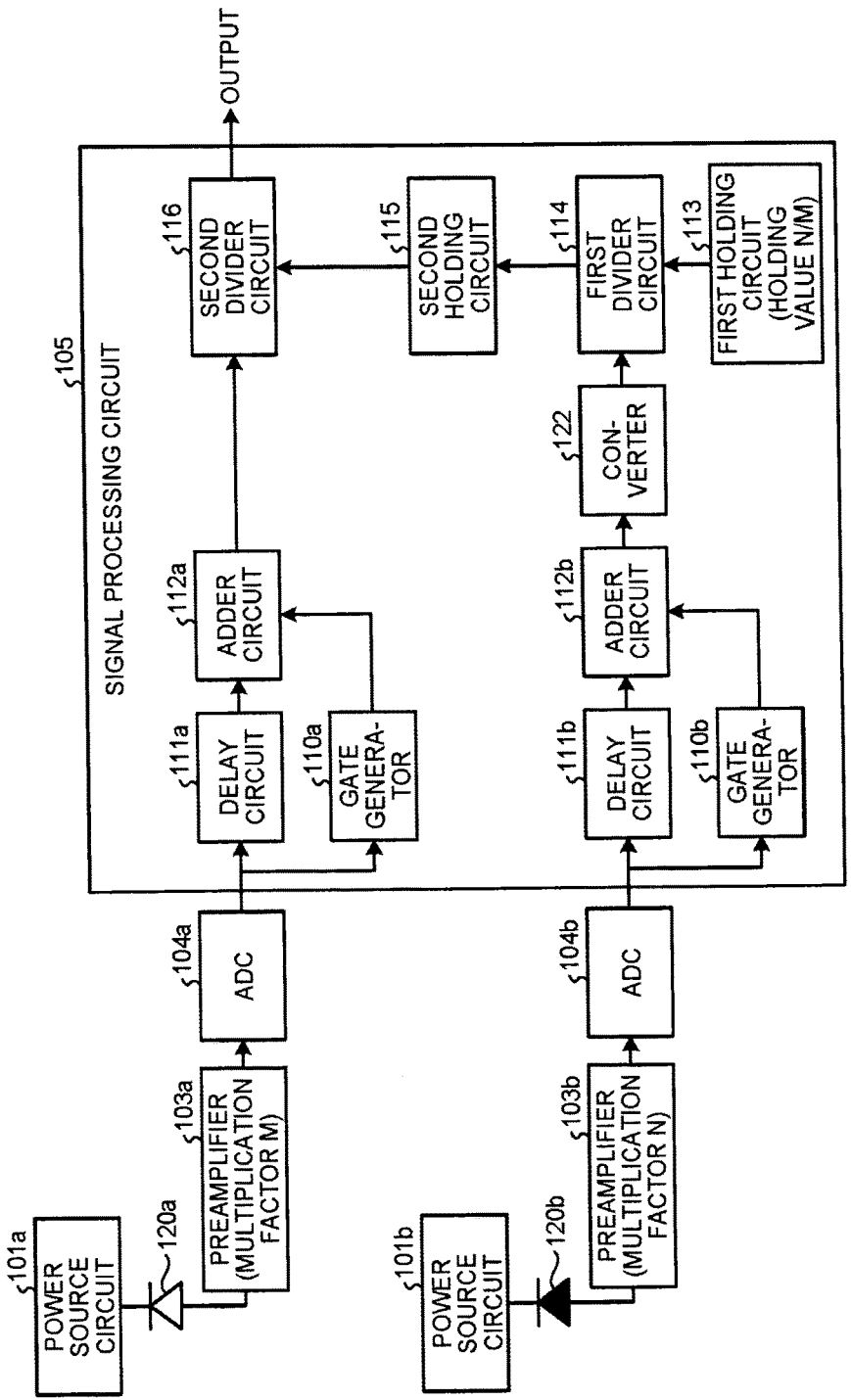
FIG. 6 is a configuration diagram exemplarily illustrating a structure of a modification of the light detection device according to the embodiment.
Figure 7:
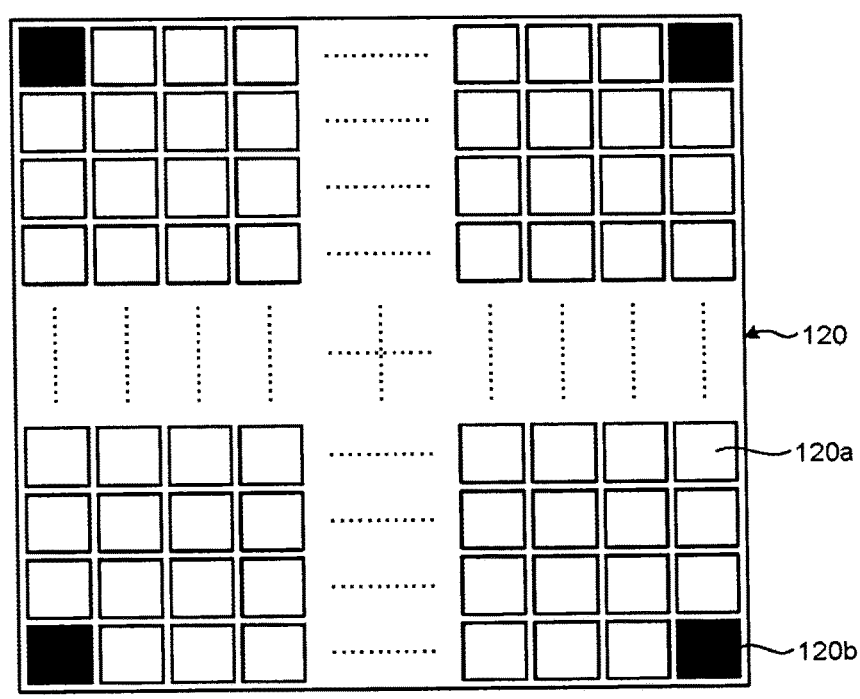
FIG. 7 is a top view of an avalanche photodiode array in the modification of the light detection device according to the embodiment.

FIG. 6 is a configuration diagram exemplarily illustrating a structure of a modification (a light detection device 100a) of the light detection device 100. FIG. 7 is a top view of an avalanche photodiode array 120 in which APDs 120a and 120b illustrated in FIG. 6 are two-dimensionally arranged. The substantially same components as the light detection device 100 illustrated in FIG. 1 out of the components of the light detection device 100a illustrated in FIG. 6 are labeled with the same numerals as the light detection device 100 illustrated in FIG. 1.

The avalanche photodiode array 120 outputs a current pulse according to the number of photons of visible light received via a scintillator (the phosphor 130, refer to FIG. 9), which is not illustrated in FIG. 7. As illustrated in FIG. 7, the avalanche photodiode array 120 includes a plurality of (e.g., about hundreds to thousands pieces of) APDs 120a and a plurality of (e.g., four) APDs 120b. The APDs 120b may be set at any position in the avalanche photodiode array 120

The APD 120a forms an APD pixel (image element) that is light sensitive and individually operates in the Geiger mode. The APD 120b forms an APD pixel (image element) that is light insensitive and individually operates in the Geiger mode. The APDs 120a and 120b are under the influence of the same environmental temperature.

Upon receiving photons of visible light, the APD 120a outputs a one photon equivalent current pulse. All of the APDs 120a are connected in parallel with one another. As a result, the current pulses output by the respective APDs 120a are superimposed to form a single current pulse. The avalanche photodiode array 120 outputs, to the preamplifier 103a, the current pulse having an area approximately proportional to the number of APDs 120a on which photons are incident. The number of APDs 120a on which photons are incident is equivalent to the number of photons of incident visible light. The area of the current pulse with respect to a temporal direction is proportional to the number of APDs 120a on which photons are incident, i.e., the total amount of generated charges.

Each of the APDs 120b is covered with a metal or the like (e.g., on the incident side of the phosphor 130) such that no visible light is incident on the APD 120b. Each APD 120b is configured to output a current pulse independently from the APDs 120a. All of the APDs 120b are connected in parallel with one another. As a result, the current pulses output by the respective APDs 120b are superimposed to form a single current pulse. The avalanche photodiode array 120, thus, outputs, to the preamplifier 103b, the current pulse having an area approximately proportional to the number of APDs 120b that generate noise.

The preamplifier 103b, the ADC 104b, the gate generator 110b, the delay circuit 111b, and the adder circuit 112b operate in the same manner as those described with reference to FIG. 1 except that an input value is not always a one photon equivalent value.

A converter 122 converts the voltage pulse output by the adder circuit 112b into a voltage pulse having a one photon equivalent waveform height, and outputs the result to the first divider circuit 114. The converter 122 determines the number of photons (the number of photon equivalents) of the voltage pulse output by the adder circuit 112b using a variation range of the area of the current pulse output by the APD 102b, where the variation range is variable in accordance with a temperature, and the area of the one photon equivalent current pulse at a reference temperature, for example. The converter 122 calculates the voltage pulse having a one photon equivalent waveform height by dividing the voltage pulse output by the adder circuit 112b by the determined number of photons. In the structure including two or more pixels and the converter, the number of voltage pulses each having the one photon equivalent waveform height that can be measured per unit time is larger than that in the structure including a single pixel. The calculation accuracy of the voltage pulse having the one photon equivalent waveform height, thus, increases.

EXAMPLE

Figure 8:
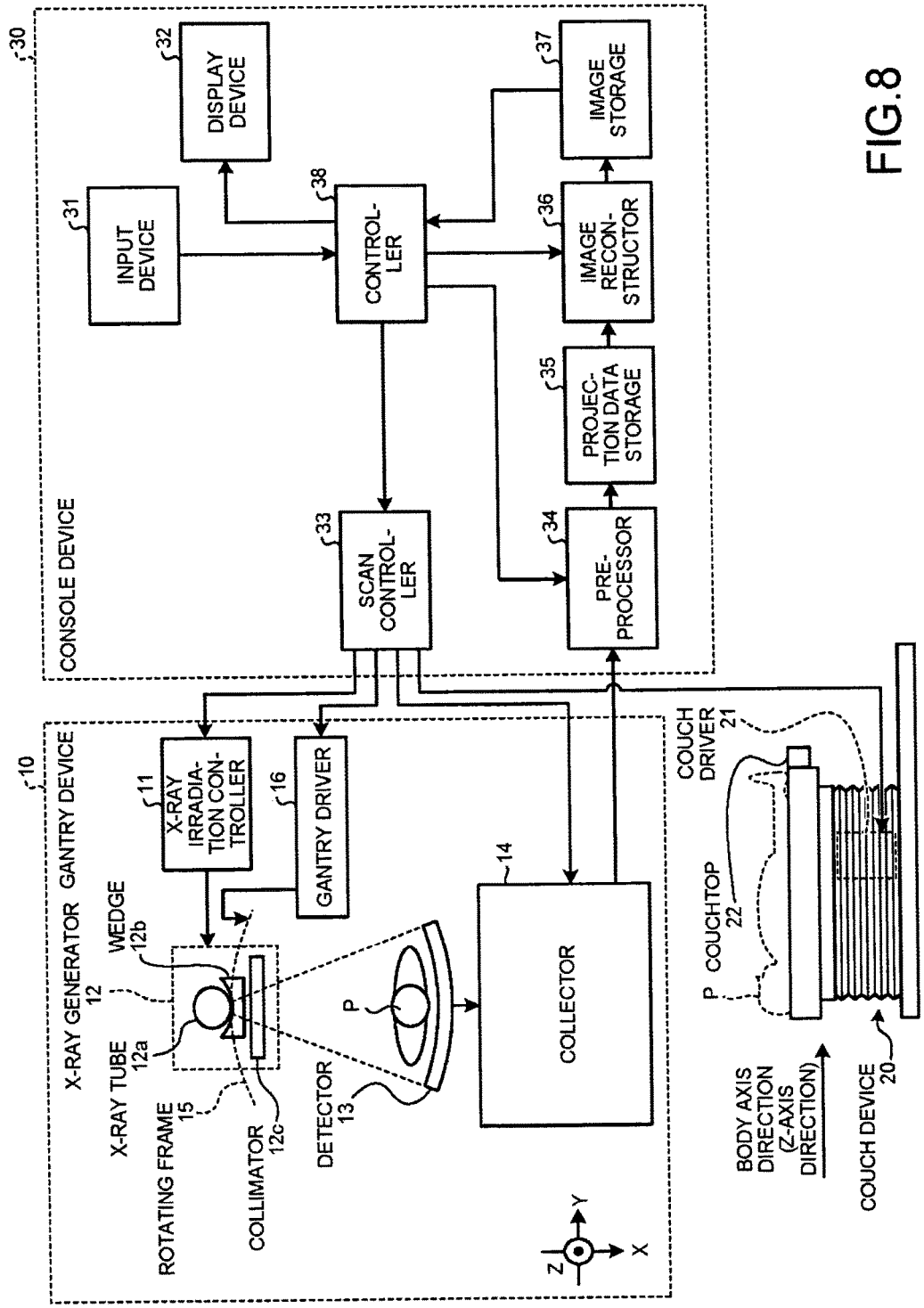
FIG. 8 is a configuration diagram illustrating an example of a structure of a radiation analysis device including the light detection device according to the embodiment.
Figure 9:
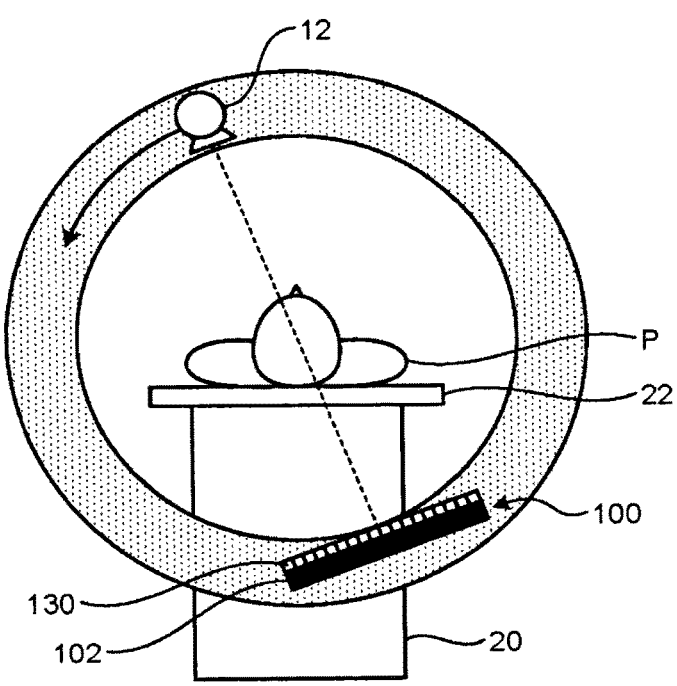
FIG. 9 is a schematic diagram schematically illustrating a position of the light detection device in the radiation analysis device illustrated in FIG. 8.

The following describes a radiation analysis device including the light detection device 100, which also serves as a radiation detection device. FIG. 8 is a configuration diagram illustrating an example of a structure of the radiation analysis device including the light detection device 100. FIG. 9 is a schematic diagram schematically illustrating a position of the light detection device 100 in the radiation analysis device illustrated in FIG. 8. The radiation analysis device is an X-ray CT apparatus that can perform photon counting CT. The radiation analysis device includes the light detection device 100 and can reconstruct X-ray CT image data having a high SN ratio by counting the number of photons generated by X-rays passing through a subject using photon counting.

Different photons have different energy. The photon counting CT can obtain information about energy components of X-rays by measuring the energy values of photons. The photon counting CT can produce images with a plurality of separated energy components from data collected from X-rays irradiation using a single tube voltage.

As illustrated in FIG. 8, the radiation analysis device includes a gantry device 10, a couch device 20, and a console device 30.

The gantry device 10 irradiates a subject P with X-rays and counts X-rays passing through the subject P. The gantry device 10 includes an X-ray irradiation controller 11, an X-ray generator 12, a detector 13 (including the light detection device 100), a collector 14, a rotating frame 15, and a gantry driver 16.

The rotating frame 15 is an annular frame that supports the X-ray generator 12 and the detector 13 such that they face each other interposing the subject P and is rotated at a high speed on a circular path around the subject P as the center by the gantry driver 16, which is described later.

The X-ray generator 12 (radiation source) generates X-rays and irradiates the subject P with the generated X-rays. The X-ray generator 12 includes an X-ray tube 12a, a wedge 12b, and a collimator 12c.

The X-ray tube 12a is a vacuum tube that irradiates the subject P with X-ray beams using a high voltage supplied by the X-ray generator 12, which is described later. The x-ray tube 12a irradiates the subject P with X-ray beams with the rotation of the rotating frame 15. The X-ray tube 12a generates X-ray beams widening with a fan angle and a corn angle.

The wedge 12b is an X-ray filter that regulates an amount of the X-rays emitted from the X-ray tube 12a. Specifically, the wedge 12b is a filter that transmits and attenuates the X-rays emitted from the X-ray tube 12a for exposure such that X-rays emitted from the X-ray tube 12a and irradiating the subject P has a predetermined distribution.

The wedge 12b is a filter made from aluminum by being processed so as to have a certain target angle and a certain thickness, for example. The wedge is also called a wedge filter or a bow-tie filter. The radiation analysis device includes a plurality of types of wedges 12b that can be switched in accordance with imaging conditions. The X-ray irradiation controller 11, which is described later, switches the wedges 12b in accordance with imaging conditions, for example. The X-ray generator 12 includes two types of wedges, for example.

The collimator 12c is a slit that narrows the irradiation area of the X-rays the amount of which is regulated by the wedge 12b under the control of the X-ray irradiation controller 11, which is described later.

The X-ray irradiation controller 11 serves as a high voltage generator to supply a high voltage to the X-ray tube 12a. The X-ray tube 12a generates X-rays using the high voltage supplied from the X-ray irradiation controller 11.

The X-ray irradiation controller 11 adjusts the amount of X-rays with which the subject P is irradiated by adjusting a tube voltage and a tube current supplied to the X-ray tube 12a.

The X-ray irradiation controller 11 switches the wedges 12b. The X-ray irradiation controller 11 adjusts the irradiation area (the fan angle and the corn angle) of X-rays by adjusting an aperture of the collimator 12c. The radiation analysis device may switch a plurality of types of wedges by the operator's manual operation.

The gantry driver 16 drives the rotating frame 15 to rotate, thereby rotating the X-ray generator 12 and the detector 13 on a circular path around the subject P as the center.

The detector 13 includes the light detection device 100 at the position illustrated in FIG. 9 and outputs a signal capable of measuring energy values of X-rays at each reception of X-rays. In the light detection device 100, the avalanche photodiode array 102 detects photons generated by X-rays incident on the phosphor 130. X-rays incident on the phosphor 130 are emitted from the X-ray tube 12a and pass through the subject P, for example. The radiation analysis device can measure, by arithmetic processing, the energy values of the radiation detected by the light detection device 100.

The collector 14 (refer to FIG. 8) collects count information that is a result of count processing using the output signal of the detector 13. The collector 14 differentiates the signals output from the detector 13 from one another and collects the count information. The count information is collected from each signal output by the detector 13 each time X-rays, which are emitted from the X-ray tube 12a and pass through the subject P, are incident on the detector 13. Specifically, the count values of the X-rays incident on the detector 13 and the energy values are associated with each other in the count information. The collector 14 transmits the collected count information to the console device 30.

The couch device 20, on which the subject P lays, includes a couchtop 22 and a couch driver 21. The couchtop 22 is a plate on which the subject P lays. The couch driver 21 moves the couchtop 22 in the Z-axis direction to move the subject P in the rotating frame 15.

The gantry device 10 implements helical scanning in which the rotating frame 15 is rotated while the couchtop 22 is moved so as to scan the subject P by a helical movement, for example. The gantry device 10 implements conventional scanning in which the rotating frame 15 is rotated while the position of the subject P is fixed so as to scan the subject P on a circular path after the couchtop 22 is moved. The gantry device 10 implements a step and shoot technique in which the conventional scan is implemented in a plurality of scan areas while the position of the couchtop 22 is inched by a constant distance.

The console device 30 receives the operator's operation on the radiation analysis device and reconstructs the X-ray CT image data using the count information collected by the gantry device 10. The console device 30 includes an input device 31, a display device 32, a scan controller 33, a preprocessor 34, a projection data storage 35, an image reconstructor 36, an image storage 37, and a controller 38.

The input device 31 includes a mouse, a keyboard, and the like that are used by the operator of the radiation analysis device to input various instructions and settings. The input device 31 transfers the instructions and information about settings received from the operator to the controller 38. The input device 31 receives, from the operator, imaging conditions of the X-ray CT image data, reconstruction conditions when the X-ray CT image data is reconstructed, and image processing conditions for the X-ray CT image data, for example.

The display device 32, which is a monitor the operator refers to, displays the X-ray CT image data to the operator and a graphical user interface (GUI) for receiving various instructions and settings from the operator via the input device 31, under the control of the controller 38.

The scan controller 33 controls the collection processing of the count information by the gantry device 10 by controlling the operation of the X-ray irradiation controller 11, the gantry driver 16, the collector 14, and the couch driver 21 under the control of the controller 38, which is described later.

The preprocessor 34 performs logarithmic conversion processing and correction processing such as offset correction, sensitivity correction, and beam hardening correction on the count information transmitted from the collector 14 to produce projection data.

The projection data storage 35 stores therein the projection data produced by the preprocessor 34. The projection data storage 35 stores therein the projection data (corrected count information) for reconstructing the X-ray CT image data. In the following description, the projection data is described as the count information in some cases.

The image reconstructor 36 reconstructs the X-ray CT image data using the projection data stored by the projection data storage 35. Various techniques are available for the reconstruction. For example, inverse projection processing is available. One of the inverse projection processing is a filtered back projection (FBP) technique, for example. The image reconstructor 36 produces the image data by performing various types of image processing on the X-ray CT image data. The image reconstructor 36 stores, in the image storage 37, the reconstructed X-ray CT image data and the image data produced by the various types of image processing.

The projection data produced from the count information obtained by the photon counting CT includes energy information about X-rays attenuated by passing through the subject P. The image reconstructor 36, thus, can reconstruct the X-ray CT image data about a specific energy component, for example. The image reconstructor 36 can reconstruct the X-ray CT image data on each of a plurality of energy components, for example.

The image reconstructor 36 can assign colors to the respective pixels of the X-ray CT image data on the respective energy components in accordance with the respective energy components to produce a plurality of pieces of X-ray CT image data colored in accordance with the respective energy components, and furthermore can produce the image data by superimposing the multiple pieces of X-ray CT image data.

Using the K-edge unique to a material, the image reconstructor 36 can produce the image data that can identify the material. An X-ray attenuation coefficient differs greatly around the K-edge, and, thus, the count value also changes greatly. The image reconstructor 36 produces the difference image data on the difference between the image data obtained by reconstructing the count information about an energy region smaller than the K-edge and the image data obtained by reconstructing the count information about an energy region larger than the K-edge, for example. For example, the difference image data produced using the K-edge of the principal component of contrast media represents an image that mainly visualizes an area where the contrast media are present. Examples of other image data produced by the image reconstructor 36 include monochrome X-ray image data, density image data, and effective atomic number image data.

The controller 38 controls the whole of the radiation analysis device by controlling the operation of the gantry device 10, the couch device 20, and the console device 30. Specifically, the controller 38 controls the CT scan operation by the gantry device 10 by controlling the scan controller 33. The controller 38 controls the image reconstruction processing and the image generation processing by the console device 30 by controlling the preprocessor 34 and the image reconstructor 36. The controller 38 performs control such that the various types of image data stored in the image storage 37 are displayed on the display device 32.

When the signal processing circuit 105 stores therein the reference table and the time series data of the voltage values corresponding to the output of the APD 102a, the light detection device 100 corrects the time series data of the voltage values corresponding to the output of the APD 102a on the basis of the environmental temperature. In this case, the image reconstructor 36 produces the image data on the basis of the time series data of the voltage values corrected by the light detection device 100, for example. The console device 30 may be structured such that the image reconstructor 36 produces two images (an image before correction and another image after correction) on the basis of the time series data of the voltage values before the correction by the light detection device 100 and the time series data of the voltage values after the correction by the light detection device 100, and the display device 32 displays the two produced images.

The light detection device 100 is used for another apparatus besides the X-ray CT apparatus described above. For example, the light detection device 100 is used for a nuclear medicine imaging apparatus such as a positron emission computed tomography (PET) apparatus or a single photon emission computed tomography (SPECT) apparatus, and a "PET-CT apparatus" and a "SPECT-CT apparatus", each of which is a combination of the X-ray CT apparatus and the nuclear medicine imaging apparatus. The light detection device 100 may be used for a light receiving unit of the PET apparatus and be included in an apparatus combined with a magnetic resonance imaging (MRI) apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photon counting CT apparatus, comprising:
   an X-ray tube configured to generate X-rays;
   a scintillator configured to convert the X-rays generated by the X-ray tube into light and emit the light;
   a photodiode array including a first pixel and a second pixel, the first pixel including a light sensitive first photodiode that is in a first range, where the light emitted from the scintillator is received, wherein the light sensitive first photodiode outputs a first electrical signal on the basis of the light, the second pixel including a light insensitive second photodiode that is in a second range located at a different position from a position of the first range, wherein the light insensitive second photodiode outputs a second electrical signal;
   a first gate generator configured to receive voltage values based on the first electrical signal and produce a gate signal;
   first delay circuitry configured to receive and delay the voltage values based on the first electrical signal;
   first adder circuitry configured to add the voltage values received from the first delay circuitry in accordance with the gate signal produced by the first gate generator;
   a second gate generator configured to receive voltage values based on the second electrical signal and produce a gate signal;
   second delay circuitry configured to receive and delay the voltage values based on the second electrical signal;
   second adder circuitry configured to add the voltage values received from the second delay circuitry in accordance with the gate signal produced by the second gate generator;
   first holding circuitry configured to hold a holding value, wherein the holding value is a ratio of an amplification factor of the first electrical signal for a period from when the first electrical signal is output from the light sensitive first photodiode to when the first electrical signal is received by the first delay circuitry and the first adder circuitry, to an amplification factor of the second electrical signal for a period from when the second electrical signal is output from the light insensitive second photodiode to when the second electrical signal is received by the second delay circuitry and the second adder circuitry;
   first divider circuitry configured to divide a value of electrical signals output by the second adder circuitry by the holding value;
   second holding circuitry configured to hold a division result by the first divider circuitry;
   second divider circuitry configured to count a number of photons of light incident on the first pixel by dividing a value of electrical signals output by the first adder circuitry by the division result held by the second holding circuitry; and
   image generator circuitry configured to reconstruct an image based on the counted number of photons of light.

2. The photon counting CT apparatus according to claim 1, wherein the second holding circuitry holds the value of the second electrical signal, which is an output value of the light insensitive second photodiode and generated due to thermal noise.

3. The photon counting CT apparatus according to claim 1, wherein
   the photodiode array includes a plurality of the second pixels,
   the apparatus further comprises converter circuitry configured to obtain a value of an electrical signal output by one of the plurality of second pixels from an integrated value of electrical signals output by the plurality of second pixels, and
   the second holding circuitry is configured to hold the value of the electrical signal obtained by the converter circuitry.

4. The photon counting CT apparatus according to claim 1, wherein the light sensitive first photodiode and the light insensitive second photodiode operate in a Geiger mode.

5. The photon counting CT apparatus according to claim 1, further comprising:

a storage to store a reference table in which an output of the light insensitive second photodiode is associated with each temperature in advance, and store time series data in which an output of the light sensitive first photodiode is associated with a temperature; and corrector circuitry configured to correct the time series data based on the reference table and the time series data stored in the storage, wherein the image generator produces an image based on the time series data corrected by the corrector circuitry.

6. A light detection device, comprising:

a photodiode array including a first pixel and a second pixel, the first pixel including a light sensitive first photodiode that is in a first range, where a light is received, wherein the light sensitive first photodiode outputs a first electrical signal on the basis of the light, the second pixel including a light insensitive second photodiode that is in a second range located at a different position from a position of the first range, wherein the light sensitive second photodiode outputs a second electrical signal;

a first gate generator configured to receive voltage values based on the first electrical signal and produce a gate signal;

first delay circuitry configured to receive and delay the voltage values based on the first electrical signal;

first adder circuitry configured to add the voltage values received from the first delay circuitry in accordance with the gate signal produced by the first gate generator;

a second gate generator configured to receive voltage values based on the second electrical signal and produce a gate signal;

second delay circuitry configured to receive and delay the voltage values based on the second electrical signal;

second adder circuitry configured to add the voltage values received from the second delay circuitry in accordance with the gate signal produced by the second gate generator;

first holding circuitry configured to hold a holding value, wherein the holding value is a ratio of an amplification factor of the first electrical signal for a period from when the first electrical signal is output from the light sensitive first photodiode to when the first electrical signal is received by the first delay circuitry and the first adder circuitry, to an amplification factor of the second electrical signal for a period from when the second electrical signal is output from the light insensitive second photodiode to when the second electrical signal is received by the second delay circuitry and the second adder circuitry;

first divider circuitry configured to divide a value of electrical signals output by the second adder circuitry by the holding value;

second holding circuitry configured to hold a division result by the first divider circuitry; and second divider circuitry configured to count a number of photons of light incident on the first pixel by dividing a value of electrical signals output by the first adder circuitry by the division result held by the second holding circuitry.

7. A radiation detection device, comprising:

a phosphor to generate the light in accordance with an energy of radiation when receiving the radiation; and the light detection device according to claim 6 to calculate the number of the photons of the light generated by the phosphor.

8. A radiation analysis device comprising:

the radiation detection device according to claim 7; and a radiation source configured to emit X-rays as the radiation to the phosphor, wherein the light detection device calculates the number of photons caused by the X-rays emitted by the radiation source.

* * * * *